(12) United States Patent
Peters et al.

(10) Patent No.: US 8,372,832 B2
(45) Date of Patent: *Feb. 12, 2013

(54) 1,4-DIAZA-BICYCLO[3.2.2]NONYL OXADIAZOLYL COMPOUNDS AND THEIR MEDICAL USE

(75) Inventors: Dan Peters, Malmö (SE); Gunnar M. Olsen, Smerum (DK); Elsebet Østergaard Nielsen, København (DK); Daniel B. Timmermann, Herlev (DK); Steven Charles Loechel, Frederiksberg (DK); Jens Damsgaard Mikkelsen, Lyngby (DK); Henrik Björk Hansen, København (DK); John Paul Redrobe, Rødovre (DK); Jeppe Kejser Christensen, København N (DK); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/420,071

(22) Filed: Mar. 14, 2012

(65) Prior Publication Data

US 2012/0172353 A1 Jul. 5, 2012

Related U.S. Application Data

(62) Division of application No. 12/297,333, filed as application No. PCT/EP2007/055168 on May 29, 2007, now Pat. No. 8,158,619.

(60) Provisional application No. 60/809,024, filed on May 30, 2006.

(30) Foreign Application Priority Data

May 30, 2006 (DK) .................................. 2006 00731

(51) Int. Cl.
*A61P 25/00* (2006.01)
*A61K 31/551* (2006.01)
*C07D 471/08* (2006.01)

(52) U.S. Cl. ...................................... 514/221; 540/556

(58) Field of Classification Search .................. 514/221; 540/556
See application file for complete search history.

(56) References Cited

U.S. PATENT DOCUMENTS

| 6,844,337 | B2 | 1/2005 | Galli et al. |
|---|---|---|---|
| 6,998,399 | B2 | 2/2006 | Galli et al. |
| 7,001,902 | B2 | 2/2006 | Gallet et al. |
| 7,022,697 | B2 | 4/2006 | Galli et al. |
| 7,220,741 | B2 | 5/2007 | Peters et al. |
| 2008/0227773 | A1 | 9/2008 | Peters et al. |

FOREIGN PATENT DOCUMENTS

| WO | WO 01/92259 A1 | 12/2001 |
|---|---|---|
| WO | WO 01/92260 A1 | 12/2001 |
| WO | WO 03/044019 A1 | 5/2003 |
| WO | WO 03/044020 A1 | 5/2003 |
| WO | WO 2004/029053 A1 | 4/2004 |
| WO | WO 2005/074940 A1 | 8/2005 |
| WO | WO 2007/138038 A1 | 12/2007 |

OTHER PUBLICATIONS

Deuther-Conrad et al., "Molecular imaging of • 7 nicotinic acetylcholine receptors: design and evaluation of the potent radioligand [18F]NS10743", European Journal of Nuclear Medicine and Molecular Imaging, vol. 36, pp. 791-800, Jan. 10, 2009.

*Primary Examiner* — Brenda Coleman
(74) *Attorney, Agent, or Firm* — Birch, Stewart, Kolasch & Birch, LLP

(57) ABSTRACT

This invention relates to novel 1,4-diaza-bicyclo[3.2.2]nonyl oxadiazolyl derivatives and their use in the manufacture of pharmaceutical compositions. The compounds of the invention are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

5 Claims, No Drawings

1,4-DIAZA-BICYCLO[3.2.2]NONYL OXADIAZOLYL COMPOUNDS AND THEIR MEDICAL USE

CROSS REFERENCE

The present application is a 35 U.S.C. §1.53(b) divisional of, and claims priority to, U.S. application Ser. No. 12/297,333, filed Oct. 16, 2008, now U.S. Pat. No. 8,158,619. Application Ser. No. 12/297,333 is the national phase under 35 U.S.C. §371 of International Application No. PCT/EP2007/055168, filed on May 29, 2007. Priority is also claimed to US Application No. 60/809,024 filed May 30, 2006 and Denmark Application No. PA 2006 00731 filed on May 30, 2006. The entire contents of each of these applications is hereby expressly incorporated by reference.

TECHNICAL FIELD

This invention relates to novel 1,4-diaza-bicyclo[3.2.2] nonyl oxadiazolyl derivatives and their use in the manufacture of pharmaceutical compositions. The compounds of the invention are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

WO 2004/029053 describes 1,4-diazabicycloalkane derivatives useful as modulators of the nicotinic and/or of the monoamine receptors. However, the 1,4-diaza-bicyclo[3.2.2] nonyl oxadiazolyl derivatives of the present invention have not been described.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel 1,4-diaza-bicyclo[3.2.2]nonyl oxadiazolyl derivatives of Formula I

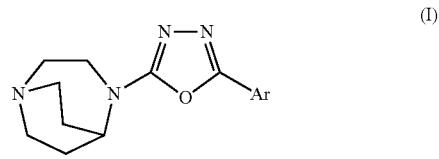

(I)

or a pharmaceutically acceptable salt thereof; wherein

Ar represents a phenyl, furanyl or thienyl group, which phenyl, furanyl and thienyl may optionally be substituted one or more times with substituents selected from alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl;

provided, however, that the 1,4-diaza-bicyclo[3.2.2]nonyl oxadiazolyl derivative is not 4-(5-Benzo[1,3]dioxol-5-yl-[1,3,4]oxadiazol-2-yl)-1,4-diaza-bicyclo[3.2.2]nonane or 4-[5-(2,3-Dihydro-benzo[1,4]dioxin-6-yl)-[1,3,4]oxadiazol-2-yl]-1,4-diaza-bicyclo[3.2.2]nonane, or a pharmaceutically acceptable salt thereof.

In its second aspect the invention provides pharmaceutical compositions comprising a therapeutically effective amount of the 1,4-diaza-bicyclo[3.2.2]nonyl oxadiazolyl derivatives of the invention, or a pharmaceutically-acceptable addition salt thereof, or a prodrug thereof, together with at least one pharmaceutically-acceptable carrier or diluent.

In a further aspect the invention relates to the use of the 1,4-diaza-bicyclo[3.2.2]nonyl oxadiazolyl derivatives of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the 1,4-diaza-bicyclo[3.2.2]nonyl oxadiazolyl derivatives of the invention.

Other objects of the invention will be apparent to the person skilled in the art from the following detailed description and examples.

DETAILED DISCLOSURE OF THE INVENTION

1,4-Diaza-bicyclo[3.2.2]nonyl Oxadiazolyl Derivatives

In a first aspect novel 1,4-diaza-bicyclo[3.2.2]nonyl oxadiazolyl derivatives are provided. The 1,4-diaza-bicyclo[3.2.2]nonyl oxadiazolyl derivatives of the invention may be represented by the general Formula I

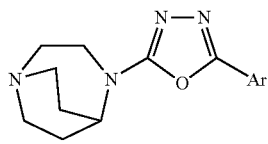

(I)

or a pharmaceutically acceptable salt thereof; wherein

Ar represents a phenyl, furanyl or thienyl group, which phenyl, furanyl and thienyl may optionally be substituted one or more times with substituents selected from alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl, provided, however, that the 1,4-diaza-bicyclo[3.2.2]nonyl oxadiazolyl derivative is not 4-(5-Benzo[1,3]dioxol-5-yl-[1,3,4]oxadiazol-2-yl)-1,4-diaza-bicyclo[3.2.2]nonane or 4-[5-(2,3-Dihydro-benzo[1,4]dioxin-6-yl)-[1,3,4]oxadiazol-2-yl]-1,4-diaza-bicyclo[3.2.2]nonane, or a pharmaceutically acceptable salt thereof.

In a preferred embodiment the 1,4-diaza-bicyclo[3.2.2]nonyl oxadiazolyl derivatives of the invention is a compound of Formula I, or a pharmaceutically acceptable salt thereof; wherein Ar represents a phenyl, furanyl or thienyl group, which phenyl, furanyl and thienyl may optionally be substituted with alkyl, cycloalkyl, cycloalkyl-alkyl, hydroxy, alkoxy, halo, trifluoromethyl, trifluoromethoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl or thienyl.

In a more preferred embodiment Ar represents a phenyl, furanyl or thienyl group, which phenyl, furanyl and thienyl may optionally be substituted with hydroxy, alkoxy, halo, trifluoromethyl, trifluoromethoxy, cyano, nitro, amino, N,N-dialkyl-amino, alkyl-sulfonyl-oxy, sulfamoyl, methylenedioxy, ethylenedioxy, furanyl or thienyl.

In an even more preferred embodiment Ar represents a phenyl, furanyl or thienyl group, which phenyl, furanyl and thienyl may optionally be substituted with hydroxy, halo, cyano, N,N-dialkyl-amino, alkyl-sulfonyl-oxy, methylenedioxy, ethylenedioxy or furanyl.

In another preferred embodiment the 1,4-diaza-bicyclo[3.2.2]nonyl oxadiazolyl derivatives of the invention is a compound of Formula I, or a pharmaceutically acceptable salt thereof; wherein Ar represents a phenyl, furanyl or thienyl group, which phenyl, furanyl and thienyl may optionally be substituted one or more times with substituents selected from hydroxy, alkoxy, halo, trifluoromethyl, trifluoromethoxy, cyano, nitro, amino, N,N-dialkyl-amino, alkyl-sulfonyl, alkyl-sulfonyl-oxy, amido, sulfamoyl, methylenedioxy, ethylenedioxy, phenyl, benzyl, furanyl and thienyl.

In a more preferred embodiment Ar represents a phenyl, furanyl or thienyl group, which phenyl, furanyl and thienyl may optionally be substituted one or more times with substituents selected from hydroxy, alkoxy, halo, trifluoromethyl, trifluoromethoxy, cyano, nitro, amino, N,N-dialkyl-amino, alkyl-sulfonyl-oxy, methylene-dioxy, ethylenedioxy, phenyl, benzyl, furanyl and thienyl.

In an even more preferred embodiment Ar represents a phenyl, furanyl or thienyl group, which phenyl, furanyl and thienyl may optionally be substituted one or more times with substituents selected from hydroxy, alkoxy, in particular methoxy, halo in particular fluoro, chloro, iodo or bromo, trifluoromethyl, cyano, nitro, amino, N,N-dialkyl-amino, alkyl-sulfonyl-oxy, in particular methylsulfonyl-oxy, methylenedioxy, ethylenedioxy and furanyl.

In a third preferred embodiment the 1,4-diaza-bicyclo[3.2.2]nonyl oxadiazolyl derivatives of the invention is a compound of Formula Ia,

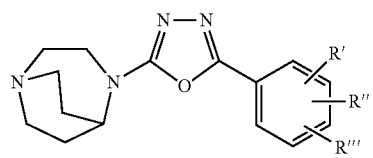

(Ia)

or a pharmaceutically acceptable salt thereof; wherein

R', R" and R'", independently of each other, represent hydrogen, alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-wry, carbamoyl, alkyl-sulfonyl, alkyl-sulfonyl-oxy, amido, sulfamoyl, methylenedioxy, ethylenedioxy, phenyl, benzyl, furanyl or thienyl.

In a more preferred embodiment R', R" and R'", independently of each other, represent hydrogen, hydroxy, alkoxy, in particular methoxy, halo, in particular fluoro, chloro, iodo or bromo, haloalkyl, in particular trifluoromethyl, cyano, nitro, amino, N,N-dialkyl-amino, alkyl-sulfonyl-oxy, in particular methylsulfonyl-oxy, methylenedioxy, ethylenedioxy, furanyl or thienyl.

In a fourth preferred embodiment the 1,4-diaza-bicyclo[3.2.2]nonyl oxadiazolyl derivatives of the invention is a compound of Formula Ib

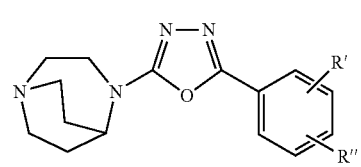

(Ib)

or a pharmaceutically acceptable salt thereof; wherein

R' and R", independently of each other, represent hydrogen, alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-wry, carbamoyl, alkyl-sulfonyl, alkyl-sulfonyl-oxy, amido, sulfamoyl, methylenedioxy, ethylenedioxy, phenyl, benzyl, furanyl or thienyl.

In a more preferred embodiment R' represents alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl; and R" represents hydrogen.

In an even more preferred embodiment R' represents hydroxy, alkoxy, halo, trifluoromethyl, cyano, nitro, amino, N,N-dialkyl-amino, alkyl-sulfonyl-oxy, sulfamoyl, methylenedioxy, ethylenedioxy, furanyl or thienyl; and R" represents hydrogen.

In a still more preferred embodiment R' represents hydroxy, halo, in particular fluoro, chloro, iodo or bromo, cyano, N,N-dialkyl-amino, alkyl-sulfonyl-oxy, in particular methylsulfonyl-oxy, methylenedioxy, ethylenedioxy or furanyl; and R" represents hydrogen.

In a yet more preferred embodiment R' represents hydroxy, fluoro, chloro, bromo, cyano, N,N-dimethyl-amino, methylsulfonyl-oxy, in particular methylsulfonyl-oxy, methylenedioxy, ethylenedioxy or furanyl; and R" represents hydrogen.

In a most preferred embodiment the 1,4-diaza-bicyclo [3.2.2]nonyl oxadiazolyl derivative of the Formula Ib is
{4-[5-(1,4-Diaza-bicyclo[3.2.2]non-4-yl)-[1,3,4]oxadiazol-2-yl]-phenyl}-dimethyl-amine;
4-[5-(4-Bromo-phenyl)-[1,3,4]oxadiazol-2-yl]-1,4-diaza-bicyclo[3.2.2]nonane;
4-[5-(3-Fluoro-phenyl)-[1,3,4]oxadiazol-2-yl]-1,4-diaza-bicyclo[3.2.2]nonane;
4-[5-(4-Fluoro-phenyl)-[1,3,4]oxadiazol-2-yl]-1,4-diaza-bicyclo[3.2.2]nonane;
4-[5-(2-Fluoro-phenyl)-[1,3,4]oxadiazol-2-yl]-1,4-diaza-bicyclo[3.2.2]nonane;
4-[5-(3-Bromo-phenyl)-[1,3,4]oxadiazol-2-yl]-1,4-diaza-bicyclo[3.2.2]nonane;
4-[5-(4-Furan-2-yl-phenyl)-[1,3,4]oxadiazol-2-yl]-1,4-diaza-bcyclo[3.2.2]nonane;
4-[5-(1,4-Diaza-bicyclo[3.2.2]non-4-yl)-[1,3,4]oxadiazol-2-yl]-phenol;
Methanesulfonic acid 4-[5-(1,4-diaza-bicyclo[3.2.2]non-4-yl)-[1,3,4]oxadiazol-2-yl]-phenyl ester;
4-[5-(1,4-Diaza-bicyclo[3.2.2]non-4-yl)-[1,3,4]oxadiazol-2-yl]-benzonitrile;
4-[5-(4-Nitro-phenyl)-[1,3,4]oxadiazol-2-yl]-1,4-diaza-bicyclo[3.2.2]nonane;
4-[5-(3,4-Dimethoxy-phenyl)-[1,3,4]oxadiazol-2-yl]-1,4-diaza-bicyclo[3.2.2]-nonane;
4-[5-(3-Trifluoromethyl-phenyl)-[1,3,4]oxadiazol-2-yl]-1,4-diaza-bicyclo[3.2.2]-nonane;
4-[5-(3,4,5-Trimethoxy-phenyl)-[1,3,4]oxadiazol-2-yl]-1,4-diaza-bicyclo[3.2.2]-nonane;
4-[5-(4-Trifluoromethyl-phenyl)-[1,3,4]oxadiazol-2-yl]-1,4-diaza-bicyclo[3.2.2]-nonane;
4-[5-(3,4-Difluoro-phenyl)-[1,3,4]oxadiazol-2-yl]-1,4-diazabicyclo[3.2.2]nonane;
4-[5-(2,4-Difluoro-phenyl)-[1,3,4]oxadiazol-2-yl]-1,4-diazabicyclo[3.2.2]nonane;
4-[5-(3-Chloro-phenyl)-[1,3,4]oxadiazol-2-yl]-1,4-diaza-bicyclo[3.2.2]nonane;
4-[5-(2-Chloro-phenyl)-[1,3,4]oxadiazol-2-yl]-1,4-diaza-bicyclo[3.2.2]nonane;
4-[5-(4-Iodo-phenyl)-[1,3,4]oxadiazol-2-yl]-1,4-diaza-bicyclo[3.2.2]nonane;
or a pharmaceutically acceptable salt thereof.

In a fifth preferred embodiment the 1,4-diaza-bicyclo [3.2.2]nonyl oxadiazolyl derivatives of the invention is a compound of Formula Ic

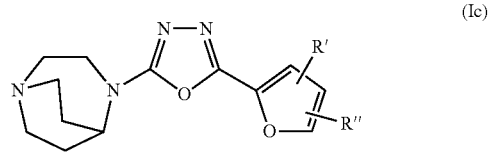

or a pharmaceutically acceptable salt thereof; wherein

R' and R", independently of each other, represent hydrogen, alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl.

In a more preferred embodiment R' represents alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl; and R" represents hydrogen.

In an even more preferred embodiment R' represents hydroxy, alkoxy, halo, trifluoromethyl, cyano, nitro, amino, N,N-dialkyl-amino, alkyl-sulfonyl-oxy, sulfamoyl, methylenedioxy, ethylenedioxy, furanyl or thienyl; and R" represents hydrogen.

In a still more preferred embodiment R' represents halo, trifluoromethyl, cyano or nitro; and R" represents hydrogen.

In a yet more preferred embodiment R' represents halo, in particular fluoro, chloro, iodo or bromo; and R" represents hydrogen.

In a further more preferred embodiment R' represents bromo; and R" represents hydrogen.

In a most preferred embodiment the 1,4-diaza-bicyclo [3.2.2]nonyl oxadiazolyl derivative of Formula Ic is
4-[5-(5-Bromo-furan-2-yl)-[1,3,4]oxadiazol-2-yl]-1,4-diaza-bicyclo[3.2.2]nonan;
or a pharmaceutically acceptable salt thereof.

In a sixth preferred embodiment the 1,4-diaza-bicyclo [3.2.2]nonyl oxadiazolyl derivatives of the invention is a compound of Formula Id

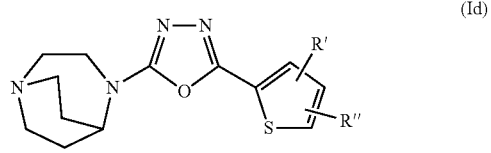

or a pharmaceutically acceptable salt thereof; wherein

R' and R", independently of each other, represent hydrogen, alkyl, cycloalkyl, cycloalkyl-alkyl, hydroxy, alkoxy, halo, haloalkyl, haloalkoxy, cyano, nitro, amino, N-alkylamino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl.

In a more preferred embodiment R' represents alkyl, cycloalkyl, cycloalkyl-alkyl, hydroxy, alkoxy, halo, haloalkyl, haloalkoxy, cyano, nitro, amino, N-alkyl-amino, N,N-dialkyl-amino, carboxy, alkyl-carbonyl, alkoxy-carbonyl, alkyl-carbonyl-oxy, carbamoyl, alkyl-sulfonyl, alkyl-sulfonyl-oxy, amido, sulfamoyl, methylenedioxy, ethylenedioxy, phenyl, benzyl, furanyl and thienyl; and R" represents hydrogen.

In an even more preferred embodiment R' represents hydroxy, alkoxy, halo, trifluoromethyl, cyano, nitro, amino, N,N-dialkyl-amino, alkyl-sulfonyl-oxy, sulfamoyl, methylenedioxy, ethylenedioxy, furanyl or thienyl; and R" represents hydrogen.

In a still more preferred embodiment R' represents halo, trifluoromethyl, cyano or nitro; and R" represents hydrogen.

In a yet more preferred embodiment R' represents halo, in particular fluoro, chloro, iodo or bromo; and R" represents hydrogen.

In a further more preferred embodiment R' represents chloro or bromo; and R" represents hydrogen.

In a most preferred embodiment the 1,4-diaza-bicyclo[3.2.2]nonyl oxadiazolyl derivative of Formula Id is
  4-[5-(5-Bromo-thiophen-2-yl)-[1,3,4]oxadiazol-2-yl]-1,4-diaza-bicyclo[3.2.2]nonane; or
  4-[5-(5-Chloro-thiophen-2-yl)-[1,3,4]oxadiazol-2-yl]-1,4-diaza-bicyclo[3.2.2]nonane;
  or a pharmaceutically acceptable salt thereof.

In a most preferred embodiment the 1,4-diaza-bicyclo[3.2.2]nonyl oxadiazolyl derivative of the invention is
  4-[5-(5-Bromo-furan-2-yl)-[1,3,4]oxadiazol-2-yl]-1,4-diaza-bicyclo[3.2.2]nonane;
  {4-[5-(1,4-Diaza-bicyclo[3.2.2]non-4-yl)-[1,3,4]oxadiazol-2-yl]-phenyl}-dimethyl-amine;
  4-[5-(4-Bromo-phenyl)-[1,3,4]oxadiazol-2-yl]-1,4-diazabicyclo[3.2.2]nonane;
  4-[5-(5-Bromo-thiophen-2-yl)-[1,3,4]oxadiazol-2-yl]-1,4-diaza-bicyclo[3.2.2]nonane;
  4-[5-(5-Chloro-thiophen-2-yl)-[1,3,4]oxadiazol-2-yl]-1,4-diaza-bicyclo[3.2.2]nonane;
  4-[5-(3-Fluoro-phenyl)-[1,3,4]oxadiazol-2-yl]-1,4-diazabicyclo[3.2.2]nonane;
  4-[5-(4-Fluoro-phenyl)-[1,3,4]oxadiazol-2-yl]-1,4-diazabicyclo[3.2.2]nonane;
  4-[5-(2-Fluoro-phenyl)-[1,3,4]oxadiazol-2-yl]-1,4-diazabicyclo[3.2.2]nonane;
  4-[5-(3-Bromo-phenyl)-[1,3,4]oxadiazol-2-yl]-1,4-diazabicyclo[3.2.2]nonane;
  4-[5-(4-Nitro-phenyl)-[1,3,4]oxadiazol-2-yl]-1,4-diazabicyclo[3.2.2]nonane;
  4-[5-(3,4-Dimethoxy-phenyl)-[1,3,4]oxadiazol-2-yl]-1,4-diaza-bicyclo[3.2.2]-nonane;
  4-[5-(3-Trifluoromethyl-phenyl)-[1,3,4]oxadiazol-2-yl]-1,4-diaza-bicyclo[3.2.2]-nonane;
  4-[5-(3,4,5-Trimethoxy-phenyl)-[1,3,4]oxadiazol-2-yl]-1,4-diaza-bicyclo[3.2.2]-nonane;
  4-[5-(4-Trifluoromethyl-phenyl)-[1,3,4]oxadiazol-2-yl]-1,4-diaza-bicyclo[3.2.2]-nonane;
  4-[5-(3,4-Difluoro-phenyl)-[1,3,4]oxadiazol-2-yl]-1,4-diazabicyclo[3.2.2]nonane;
  4-[5-(2,4-Difluoro-phenyl)-[1,3,4]oxadiazol-2-yl]-1,4-diazabicyclo[3.2.2]nonane;
  4-[5-(3-Chloro-phenyl)-[1,3,4]oxadiazol-2-yl]-1,4-diazabicyclo[3.2.2]nonane;
  4-[5-(2-Chloro-phenyl)-[1,3,4]oxadiazol-2-yl]-1,4-diazabicyclo[3.2.2]nonane;
  4-[5-(4-Iodo-phenyl)-[1,3,4]oxadiazol-2-yl]-1,4-diaza-bicyclo[3.2.2]nonane;
  4-[5-(4-Furan-2-yl-phenyl)-[1,3,4]oxadiazol-2-yl]-1,4-diaza-bcyclo[3.2.2]nonane;
  4-[5-(1,4-Diaza-bicyclo[3.2.2]non-4-yl)-[1,3,4]oxadiazol-2-yl]-phenol;
  Methanesulfonic acid 4-[5-(1,4-diaza-bicyclo[3.2.2]non-4-yl)-[1,3,4]oxadiazol-2-yl]-phenyl ester;
  4-[5-(1,4-Diaza-bicyclo[3.2.2]non-4-yl)-[1,3,4]oxadiazol-2-yl]-benzonitrile; or
  4-[5-(1,4-Diaza-bicyclo[3.2.2]non-4-yl)-[1,3,4]oxadiazol-2-yl]-phenylamine fumaric acid salt;
  or a pharmaceutically acceptable salt thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O-" group, wherein alkyl is as defined above. Examples of preferred alkoxy groups of the invention include methoxy and ethoxy.

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined herein, which alkyl group is substituted one or more times with halo. Preferred haloalkyl groups of the invention include trihalomethyl, preferably trifluoromethyl.

In the context of this invention a haloalkoxy group designates an alkoxy group as defined herein, which alkoxy group is substituted one or more times with halo. Preferred haloalkoxy groups of the invention include trihalomethoxy, preferably trifluoromethoxy.

In the context of this invention an N-alkyl-amino group designates a (secondary) amino group, monosubstituted with an alkyl group as defined above.

In the context of this invention an N,N-dialkyl-amino group designates a (tertiary) amino group, disubstituted with alkyl groups as defined above.

In the context of this invention an alkyl-carbonyl group designates an "alkyl-CO— group", wherein alkyl is as defined above. Examples of preferred alkyl-carbonyl groups of the invention include acetyl and propionyl.

In the context of this invention an alkoxy-carbonyl group designates an "alkyl-O—CO—" group, wherein alkyl is as defined above. Examples of preferred alkoxy-carbonyl groups of the invention include the methyl-, ethyl-and propyl-ester group.

In the context of this invention an alkyl-carbonyl-oxy group designates an "alkyl-CO—O—" group, wherein alkyl is as defined above. Examples of preferred alkyl-carbonyl-oxy groups of the invention include acetoxy and propionyloxy.

In the context of this invention an alkyl-sulfonyl group designates an "alkyl-SO$_2$—" group, wherein alkyl is as defined above. Examples of preferred alkyl-sulfonyl groups of the invention include methyl-sulfonyl, ethyl-sulfonyl and propyl-sulfonyl.

In the context of this invention an alkyl-sulfonyl-oxy designates an "alkyl-SO$_2$—O—" group, wherein alkyl is as defined above. Examples of preferred alkyl-sulfonyl-oxy groups of the invention include methyl-sulfonyl-oxy, ethyl-sulfonyl-oxy and propyl-sulfonyl-oxy.

Pharmaceutically Acceptable Salts

The 1,4-diaza-bicyclo[3.2.2]nonyl oxadiazolyl derivative of the invention may be provided in any form suitable for the intended administration. Suitable forms include pharmaceutically (i.e. physiologically) acceptable salts, and pre-or pro-drug forms of the compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzene-sulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a 1,4-diaza-bicyclo[3.2.2]nonyl oxadiazolyl derivatives of the invention and its pharmaceutically acceptable acid addition salt.

Examples of pharmaceutically acceptable cationic salts of a 1,4-diaza-bicyclo[3.2.2]nonyl oxadiazolyl derivative of the invention include, without limitation, the sodium, the potassium, the calcium, the magnesium, the zinc, the aluminium, the lithium, the choline, the lysine, and the ammonium salt, and the like, of a compound of the invention containing an anionic group. Such cationic salts may be formed by procedures well known and described in the art.

Additional examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a 1,4-diaza-bicyclo[3.2.2]nonyl oxadiazolyl derivative of the invention include alkali metal salts, such as the sodium salt of a compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), and combinations thereof.

Methods of Producing 1,4-Diaza-bicyclo[3.2.2]nonyl Oxadiazolyl Derivatives

The 1,4-diaza-bicyclo[3.2.2]nonyl oxadiazolyl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The compounds of the invention are found to be cholinergic ligands at the nicotinic acetylcholine receptors and modulators of the monoamine receptors and transporters. In a more preferred embodiment the invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the present invention may be useful for the treatment, prevention or alleviation of a cognitive disorder, learning deficit, memory deficits and dysfunction, Down's syndrome, Alzheimer's disease, attention deficit, attention deficit hyperactivity disorder (ADHD), Tourette's syndrome, psychosis, depression, Bipolar Disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, fibromyalgia, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compounds of the invention may be useful for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the compounds of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a still more preferred embodiment the compounds of the invention may be useful for the treatment, prevention or alleviation of a neurodegenerative disorder, transient anoxia, or induced neuro-degeneration.

In a yet more preferred embodiment the compounds of the invention may be useful for the treatment, prevention or alleviation of an inflammatory disorder, inflammatory skin disorder, acne, rosacea, Chron's disease, inflammatory bowel disease, ulcerative colitis, or diarrhoea.

In a further preferred embodiment the compounds of the invention may be useful for the treatment, prevention or alleviation of diabetic neuropathy, schizophrenia, cognitive or attentional deficits related to schizophrenia, or depression.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the 1,4-diaza-bicyclo[3.2.2]nonyl oxadiazolyl derivative of the invention.

While a 1,4-diaza-bicyclo[3.2.2]nonyl oxadiazolyl derivative of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 1,4-diaza-bicyclo [3.2.2]nonyl oxadiazolyl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The 1,4-diaza-bicyclo[3.2.2]nonyl oxadiazolyl derivative of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The 1,4-diaza-bicyclo[3.2.2]nonyl oxadiazolyl derivative of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from a 1,4-diaza-bicyclo[3.2.2]nonyl oxadiazolyl derivative of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The 1,4-diaza-bicyclo[3.2.2]nonyl oxadiazolyl derivative according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the 1,4-diaza-bicyclo[3.2.2]nonyl oxadiazolyl derivative of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The 1,4-diaza-bicyclo[3.2.2]nonyl oxadiazolyl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a 1,4-diaza-bicyclo[3.2.2]nonyl oxadiazolyl derivative of the invention.

In a preferred embodiment, the disease, disorder or condition relates to the central nervous system.

The preferred medical indications contemplated according to the invention are those stated above.

It is at present contemplated that suitable dosage ranges are within 0.1 to 1000 milligrams daily, preferably 10 to 500 milligrams daily, and more preferred of from 30 to 100 milligrams daily, dependent as usual upon the exact mode of administration, form in which administered, the indication toward which the administration is directed, the subject involved, the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

1,4-Diazabicyclo[3.2.2]nonane (Intermediate Compound)

The title compound was prepared according to *J. Med. Chem.* 1993 36 2311-2320 (and according to the slightly modified method described below).

1,4-Diazabicyclo[3.2.2]nonane (Intermediate Compound)

To the solution of 1,4-diazabicyclo[3.2.2]nonan-3-one (15.8 g; 113 mmol) in absolute dioxane (130 ml) LiAlH$_4$ (4.9 g; 130 mmol) was added under argon. The mixture was refluxed for 6 hours and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one (Intermediate Compound)

To the solution of 3-quinuclidinone hydrochloride (45 g; 278 mmol) in 90 ml of water hydroxylamine hydrochloride (21 g; 302 mmol) and sodium acetate (CH$_3$COOHx3H$_2$O; 83 g; 610 mmol) were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions to preheated to 120° C. polyphosphoric acid (190 g). The temperature of the solution during the reaction was kept at 130° C. After addition of all oxime the solution was stirred for 20 minutes at the same temperature, then transferred to an enamelled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp. 211-212° C.

Method A

4-[5-(5-Bromo-furan-2-yl)-[1,3,4]oxadiazol-2-yl]-1,4-diaza-bicyclo[3.2.2]nonane Free Base (Compound A1)

A mixture of 1,4-diazabicyclo[3.2.2]nonane (4.05 g, 32.1 mmol), 2-benzylsulfanyl-5-(5-bromo-furan-2-yl)-[1,3,4] oxadiazole (10.3 g, 30.5 mmol) and N,N-diisopropylethylamine (8.29 g, 64.1 mmol) was stirred at 100° C. for 4 hours. Aqueous sodium hydroxide (30 ml, 1 M) was added followed by extraction with chloroform (3×30 ml). The organic phase was dried and evaporated. The crude solid mixture was solved in hot ethyl acetate (100 ml), some red, glue-like impurities where removed by filtration. The filtrate was evaporated and finally the crystalline product was triturated with diethylether. Yield 3.43 g (33%). LC-ESI-HRMS of [M+H]+ shows 339.0453 Da. Calc. 339.045664 Da, dev. −1.1 ppm.

{4-[5-(1,4-Diaza-bicyclo[3.2.2]non-4-yl)-[1,3,4] oxadiazol-2-yl]-phenyl}-dimethyl-amine Fumaric Acid Salt (Compound A2)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. Mp 170.9-171.8° C.

4-[5-(4-Bromo-phenyl)-[1,3,4]oxadiazol-2-yl]-1,4-diaza-bicyclo[3.2.2]nonane Hydrochloric Acid Salt (Compound A3)

Was prepared according to Method A. Chromatography on silica gel with chloroform, 10% methanol and 1% aqueous ammonia as solvent gave the title compound. The corresponding salt was obtained by addition of hydrochloric acid in ethanol Mp 287° C. (dec.).

4-[5-(5-Bromo-thiophen-2-yl)-[1,3,4]oxadiazol-2-yl]-1,4-diaza-bicyclo[3.2.2]nonane Hydrochloric Acid Salt (Compound A4)

Was prepared according to Method A. Chromatography on silica gel with chloroform, 10% methanol and 1% aqueous ammonia as solvent gave the title compound. The corresponding salt was obtained by addition of hydrochloric acid in ethanol. LC-ESI-HRMS of [M+H]+ shows 355.0234 Da. Calc. 355.02282 Da, dev. 1.6 ppm.

4-[5-(5-Chloro-thiophen-2-yl)-[1,3,4]oxadiazol-2-yl]-1,4-diaza-bicyclo[3.2.2]nonane Hydrochloric Acid Salt (Compound A5)

Was prepared according to Method A. Chromatography on silica gel with chloroform, 10% methanol and 1% aqueous ammonia as solvent gave the title compound. The corresponding salt was obtained by addition of hydrochloric acid in ethanol. LC-ESI-HRMS of [M+H]+ shows 311.0722 Da. Calc. 311.073335 Da, dev. −3.6 ppm.

4-[5-(3-Fluoro-phenyl)-[1,3,4]oxadiazol-2-yl]-1,4-diaza-bicyclo[3.2.2]nonane Hydrochloric Acid Salt (Compound A6)

Was prepared according to Method A. Chromatography on silica gel with chloroform, 10% methanol and 1% aqueous ammonia as solvent gave the title compound. The corresponding salt was obtained by addition of hydrochloric acid in ethanol. LC-ESI-HRMS of [M+H]+ shows 289.1457 Da. Calc. 289.146464 Da, dev. −2.6 ppm.

4-[5-(4-Fluoro-phenyl)-[1,3,4]oxadiazol-2-yl]-1,4-diaza-bicyclo[3.2.2]nonane Free Base (Compound A7)

Was prepared according to Method A. Chromatography on silica gel with chloroform, 10% methanol and 1% aqueous ammonia as solvent gave the title compound. LC-ESI-HRMS of [M+H]+ shows 289.1454 Da. Calc. 289.146464 Da, dev. −3.7 ppm.

4-[5-(2-Fluoro-phenyl)-[1,3,4]oxadiazol-2-yl]-1,4-diaza-bicyclo[3.2.2]nonane Free Base (Compound A8)

Was prepared according to Method A. Chromatography on silica gel with chloroform, 10% methanol and 1% aqueous ammonia as solvent gave the title compound. LC-ESI-HRMS of [M+H]+ shows 289.1473 Da. Calc. 289.146464 Da, dev. 2.9 ppm.

4-[5-(3-Bromo-phenyl)-[1,3,4]oxadiazol-2-yl]-1,4-diaza-bicyclo[3.2.2]nonane Fumaric Acid Salt (Compound A9)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 349.0663 Da. Calc. 349.066399 Da, dev. −0.3 ppm.

4-[5-(4-Nitro-phenyl)-[1,3,4]oxadiazol-2-yl]-1,4-diaza-bicyclo[3.2.2]nonane Free Base (Compound A10)

Was prepared according to Method A. Chromatography on silica gel with chloroform, 10% methanol and 1% aqueous ammonia as solvent gave the title compound. LC-ESI-HRMS of [M+H]+ shows 316.1409 Da. Calc. 316.140965 Da, dev. −0.2 ppm.

4-[5-(3,4-Dimethoxy-phenyl)-[1,3,4]oxadiazol-2-yl]-1,4-diaza-bicyclo[3.2.2]-nonane Fumaric Acid Salt (Compound A11)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 331.1773 Da. Calc. 331.177016 Da, dev. 0.9 ppm.

4-[5-(3-Trifluoromethyl-phenyl)-[1,3,4]oxadiazol-2-yl]-1,4-diaza-bicyclo[3.2.2]-nonane Fumaric Acid Salt (Compound A12)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 339.1443 Da. Calc. 339.14327 Da, dev. 3 ppm.

4-[5-(3,4,5-Trimethoxy-phenyl)-[1,3,4]oxadiazol-2-yl]-1,4-diaza-bicyclo[3.2.2]-nonane Fumaric Acid Salt (Compound A13)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 361.1858 Da. Calc. 361.187581 Da, dev. −4.9 ppm.

4-[5-(4-Trifluoromethyl-phenyl)-[1,3,4]oxadiazol-2-yl]-1,4-diaza-bicyclo[3.2.2]-nonane Fumaric Acid Salt (Compound A14)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 339.142 Da. Calc. 339.14327 Da, dev. −3.7 ppm.

4-[5-(3,4-Difluoro-phenyl)-[1,3,4]oxadiazol-2-yl]-1,4-diazabicyclo[3.2.2]nonane Fumaric Acid Salt (Compound A15)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 307.1365 Da. Calc. 307.137042 Da, dev. −1.8 ppm.

4-[5-(2,4-Difluoro-phenyl)-[1,3,4]oxadiazol-2-yl]-1,4-diazabicyclo[3.2.2]nonane Fumaric Acid Salt (Compound A16)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 307.1377 Da. Calc. 307.137042 Da, dev. 2.1 ppm.

4-[5-(3-Chloro-phenyl)-[1,3,4]oxadiazol-2-yl]-1,4-diaza-bicyclo[3.2.2]nonane Fumaric Acid Salt (Compound A17)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 305,1171 Da. Calc. 305,116914 Da, dev. 0.6 ppm.

4-[5-(2-Chloro-phenyl)-[1,3,4]oxadiazol-2-yl]-1,4-diaza-bicyclo[3.2.2]nonane Fumaric Acid Salt (Compound A18)

Was prepared according to Method A. Chromatography on silica gel with chloroform, 10% methanol and 1% aqueous ammonia as solvent gave the title compound. The corresponding salt was obtained by addition of a diethyl ether and methanol mixture (9:1) saturated with fumaric acid. LC-ESI-HRMS of [M+H]+ shows 305,1164 Da. Calc. 305,116914 Da, dev. −1.7 ppm.

4-[5-(4-Iodo-phenyl)-[1,3,4]oxadiazol-2-yl]-1,4-diaza-bicyclo[3.2.2]nonane Free Base (Compound A19)

Was prepared according to Method A. Chromatography on silica gel with chloroform, 10% methanol and 1% aqueous ammonia as solvent gave the title compound. LC-ESI-HRMS ordered from CS.

Method B

2-Benzylsulfanyl-5-(5-bromo-furan-2-yl)-[1,3,4]oxadiazole (Intermediate Compound)

Benzylbromide (6.18 g, 36.1 mmol) was added over 5 minutes time-period to a mixture of 5-(5-bromo-furan-2-yl)-

[1,3,4]oxadiazole-2-thiol (8.5 g, 36.1 mmol), trietylamine (6.96 g, 68.8 mmol) and ethanol (100 ml, 99%). The reaction mixture was stirred at room-temperature for 2 hours. Aqueous sodium hydroxide (50 ml, 1 M) and water (100 ml) was added followed by extraction with diethylether (3×50 ml). The organic phase was washed with water (3×50 ml), dried and evaporated. The product was isolated as a red solid. Yield 10.7 g (92%).
Method C 5-(5-Bromo-furan-2-yl)-[1,3,4]oxadiazole-2-thiol (Intermediate Compound)

5-Bromo-furan-2-carboxylic acid hydrazide (20.5 g, 100 mmol) was added to a mixture of potassium hydroxide (6.2 g, 110 mmol) and methanol (125 ml). The mixture was stirred for 30 minutes at room temperature. Carbon disulfide (15.2 g, 200 mmol) was added. The mixture was stirred at reflux for 30 hours. Water (60 ml) was added and the excess of carbon disulfide and methanol was evaporated. The aqueous suspension was acidified by adding concentrated hydrochloric acid (14 ml). The product precipitated and was washed with water (20 ml), dried and evaporated. Yield 8.58 g (35%).
Method D 5-Bromo-furan-2-carboxylic Acid Hydrazide (Intermediate Compound)

A mixture of 5-bromo-furan-2-carboxylic acid (38.2 g, 200 mmol) and thionylchloride (163.1 g, 1.37 mol) was stirred at 70° C. overnight. The mixture of 5-bromo-furan-2-carbonyl chloride was evaporated, solved in tetrahydrofuran (10 ml) and added to a mixture of hydrazine monohydrate (120.1 g, 2.4 mol), followed by stirring for 0.5 hours at <5° C. Water (50 ml) was added followed by filtration. The crystalline product was recrystallized from ethanol (125 ml, 96%). Yield 21.2 g (52%).
Method E 4-[5-(4-Furan-2-yl-phenyl)-[1,3,4]oxadiazol-2-yl]-1,4-diaza-bcyclo[3.2.2]nonane Hydrochloric Acid Salt (Compound E1)

A mixture of 4-[5-(4-bromo-phenyl)-[1,3,4]oxadiazol-2-yl]-1,4-diaza-bicyclo[3.2.2]nonane (1.54 g, 4.0 mmol), furan-2-boronic acid (0.90 g, 8.0 mmol), bis(triphenylphosphine)palladium(II)chloride (84 mg, 0.12 mmol), potassium carbonate (1.66 g, 12.0 mmol), water (40 ml) and 1,2-dimethoxyethane (40 ml) was stirred at reflux for 15 hours. Water (50 ml) was added and the mixture was extracted with diethylether (3×100 ml). The crude mixture was purified by column chromatography on silica gel with dichloromethane, 10% methanol and 1% aqueous ammonia as solvent and gave the title compound as an oil. The corresponding salt was obtained by addition of hydrochloric acid in ethanol (5 ml, 4 M). The hydrochloric acid salt was isolated by filtration as a solid. Mp >275° C.
Method F 4-[5-(1,4-Diaza-bicyclo[3.2.2]non-4-yl)-[1,3,4]oxadiazol-2-yl]-phenol Free Base (Compound F1)

A mixture of 4-[5-(4-methoxy-phenyl)-[1,3,4]oxadiazol-2-yl]-1,4-diaza-bicyclo[3.2.2]nonane (1.0 g, 3.3 mmol) and chloroform (20 ml) was cooled to −63° C. A mixture of boron tribromide (5.4 g, 21.6 mmol) and chloroform (10 ml) was added at 60° C. The mixture was allowed to reach room-temperature. The crude mixture was purified by column chromatography on silica gel with dichloromethane, 10% methanol and 1% aqueous ammonia as solvent and gave the title compound. LC-ESI-HRMS of [M+H]+ shows 287.1514 Da. Calc. 287.150801 Da, dev. 2.1 ppm.
Method G Methanesulfonic Acid 4-[5-(1,4-diaza-bicyclo[3.2.2]non-4-yl)-[1,3,4]oxadiazol-2-yl]-phenyl Ester Fumaric Acid Salt (Compound G1)

4-[5-(1,4-Diaza-bicyclo[3.2.2]non-4-yl)-[1,3,4]oxadiazol-2-yl]-phenol free base (0.15 g, 0.52 mmol) and chloroform (20 ml) was cooled to 0° C. and N,N-diisopropylamine (0.67 g, 5.2 mmol), followed by methylsulphonylchloride (0.90 g, 7.9 mmol) was added to the mixture. The mixture was stirred for 10 days at room temperature. Aqueous sodium hydroxide (30 ml, 1 M) was added followed by extraction with chloroform (3×30 ml). Chromatography on silica gel with dichloromethane, 5% methanol and 0.5% aqueous ammonia as solvent gave the title compound as an oil. The corresponding salt was obtained by addition of a diethyl ether and methanol mixture (9:1) saturated with fumaric acid. Yield 63 mg (17%). LC-ESI-HRMS of [M+H]+ shows 365.1288 Da. Calc. 365.128352 Da, dev. 1.2 ppm.

4-[5-(1,4-Diaza-bicyclo[3.2.2]non-4-yl)-[1,3,4]oxadiazol-2-yl]-benzonitrile Hydrochloric Acid Salt (Compound G2)

A mixture of 4-[5-(4-bromo-phenyl)-[1,3,4]oxadiazol-2-yl]-1,4-diaza-bicyclo[3.2.2]nonane (1.47 g, 5.00 mmol), sodium cyanide (0.49 g, 10.0 mmol), nickel(II)bromide (1.1 g, 5.03 mmol) and NMP (15 ml) was reacted at 200° C. for 15 minutes. Water (50 ml) was added and the mixture was extracted with dichloromethane (3×50 ml). The mixture was dried and evaporated. Calcium chloride (30 ml, 3 M) was added followed by extraction with ethylacetate (3×30 ml). The mixture was dried and evaporated. The corresponding salt was obtained by addition of hydrochloric acid in ethanol. The hydrochloric acid salt was isolated by filtration as a solid. Yield 0.54 g (36%).
Method H 4-[5-(1,4-Diaza-bicyclo[3.2.2]non-4-yl)-[1,3,4]oxadiazol-2-yl]-phenylamine Fumaric Acid Salt (Compound H1)

A mixture of 4-[5-(4-nitro-phenyl)-[1,3,4]oxadiazol-2-yl]-1,4-diaza-bicyclo[3.2.2]nonane (0.60 g, 1.90 mmol), Raney Nickel, aqueous suspension (0.5 ml) and methanol (100 ml) was stirred under hydrogen. Chromatography on silica gel with chloroform, 10% methanol and 1% aqueous ammonia as solvent gave the title compound as an oil. The corresponding salt was obtained by addition of a diethyl ether and methanol mixture (9:1) saturated with fumaric acid. Yield 240 mg (31%). LC-ESI-HRMS of [M+H]+ shows 286.1662 Da. Calc. 286.166785 Da, dev. −2 ppm.

Example 2

In Vitro Inhibition of $^3$H-α-Bungarotoxine Binding in Rat Brain

In this example the affinity of a 1,4-diaza-bicyclo[3.2.2] nonyl oxadiazolyl derivative of the invention for binding to $α_7$-subtype of nicotinic receptors is determined in a standard assay carried out essentially as described in e.g. WO 2006/087306.

The test value is presented as an IC$_{50}$ (the concentration of the test substance which inhibits the specific binding of $^3$H-α-bungarotoxin by 50%).

The result of this experiment is presented in Table 1 below.

TABLE 1

| Inhibition of $^3$H-α-Bungarotoxine Binding | |
|---|---|
| Compound No. | IC$_{50}$ (μM) |
| A1 | <0.01 |

The invention claimed is:

1. A 1,4-diaza-bicyclo[3.2.2]nonyl oxadiazolyl compound of Formula I

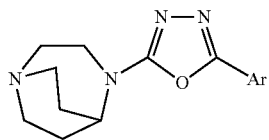

wherein Ar represents a fluoro-substituted phenyl group, or a pharmaceutically acceptable salt thereof.

2. The 1,4-diaza-bicyclo[3.2.2]nonyl oxadiazolyl compound of claim 1, which is 4-[5-(2-fluorophenyl)-[1,3,4]oxadiazol-2-yl]-1,4-diaza-bicyclo[3.2.2]nonane;

or a pharmaceutically acceptable salt thereof.

3. The 1,4-diaza-bicyclo[3.2.2]nonyl oxadiazolyl compound of claim 1, which is 4-[5-(3-fluorophenyl)-[1,3,4]oxadiazol-2-yl]-1,4-diaza-bicyclo[3.2.2]nonane;

or a pharmaceutically acceptable salt thereof.

4. The 1,4-diaza-bicyclo[3.2.2]nonyl oxadiazolyl compound of claim 1, which is 4-[5-(4-fluorophenyl)-[1,3,4]oxadiazol-2-yl]-1,4-diaza-bicyclo[3.2.2]nonane;

or a pharmaceutically acceptable salt thereof.

5. A pharmaceutical composition comprising a therapeutically effective amount of the 1,4-diaza-bicyclo[3.2.2]nonyl oxadiazolyl compound of claim 1, or pharmaceutically-acceptable addition salt thereof, together with at least one pharmaceutically acceptable carrier or diluent.

* * * * *